United States Patent [19]

Sugiyama et al.

[11] Patent Number: 4,637,256
[45] Date of Patent: Jan. 20, 1987

[54] ULTRASONIC PROBE HAVING DUAL-MOTION TRANSDUCER

[75] Inventors: Yoshiyuki Sugiyama, Ayase; Shinichiro Aoki, Kawasaki; Yasuyuki Morita, Yokohama, all of Japan

[73] Assignee: Matsushita Electric Industrial Co., Ltd., Osaka, Japan

[21] Appl. No.: 623,752

[22] Filed: Jun. 22, 1984

[30] Foreign Application Priority Data

Jun. 23, 1983 [JP] Japan ................. 58-113707
Sep. 27, 1983 [JP] Japan ................. 58-178529
Dec. 5, 1983 [JP] Japan ................. 58-229310

[51] Int. Cl.$^4$ .................. G01N 29/04; A61C 19/04; A61B 10/00
[52] U.S. Cl. ........................ 73/633; 73/621; 128/660; 433/215
[58] Field of Search ............ 73/618, 619, 620, 621, 73/622, 623, 633, 634; 128/660; 433/215

[56] References Cited

U.S. PATENT DOCUMENTS

| | | |
|---|---|---|
| 3,425,507 | 2/1969 | Caldwell et al. |
| 3,454,923 | 7/1969 | Currie ................. 367/173 |
| 3,553,638 | 1/1971 | Sublett ................ 367/173 |
| 3,845,463 | 10/1974 | Timbs ................. 73/623 |
| 4,271,706 | 1/1981 | Ledley ................ 128/660 |
| 4,282,755 | 8/1981 | Gardineer et al. ..... 73/634 |
| 4,517,985 | 5/1985 | Teslawski et al. ..... 128/660 |

FOREIGN PATENT DOCUMENTS

| | | |
|---|---|---|
| 0032751 | 7/1981 | European Pat. Off. |
| 1072161 | 12/1959 | Fed. Rep. of Germany ...... 367/173 |
| 2305501 | 8/1974 | Fed. Rep. of Germany ...... 128/660 |
| 58-185139 | 10/1983 | Japan . |
| 1112628 | 5/1968 | United Kingdom . |
| 2067759 | 7/1981 | United Kingdom . |

*Primary Examiner*—Howard A. Birmiel
*Assistant Examiner*—John E. Chapman, Jr.
*Attorney, Agent, or Firm*—Pollock, VandeSande & Priddy

[57] ABSTRACT

In a mechanically scanned ultrasonic probe, an ultrasonic transducer is swingably mounted on a drive shaft which is given a swinging transversal movement and a reciprocating longitudinal movement. The transducer emits an acoustic beam which is steered in a raster format in response to the swing and reciprocating motions. Echos returning from objects contain diagnostic data of a three-dimensional space. All the components are encased in a toothbrush-like housing having a head portion, an intermediate portion and a hand-grip portion. The dual motions are provided by a drive mechanism accommodated in the hand-grip portion and the transducer is accommodated in the head portion. The drive shaft extends through the intermediate portion.

12 Claims, 7 Drawing Figures

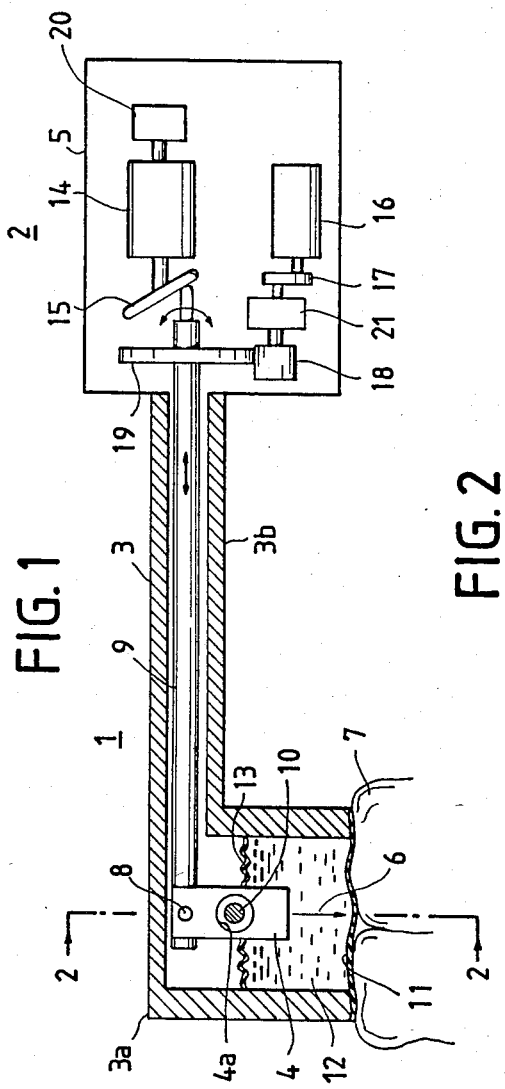
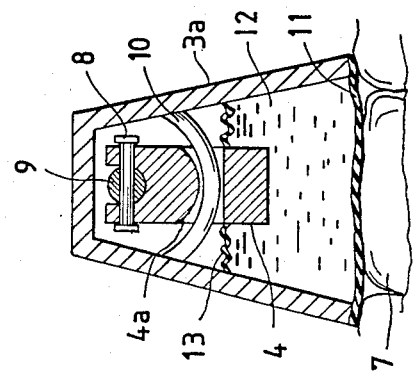

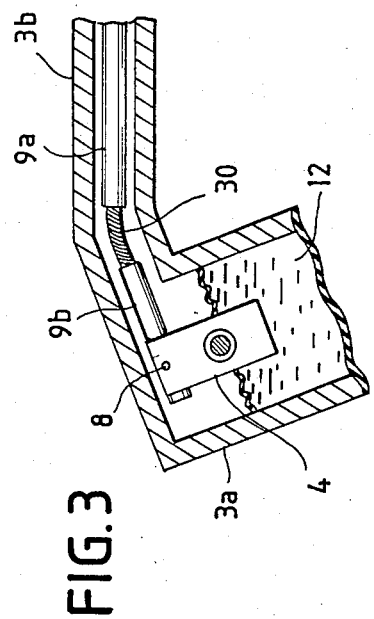
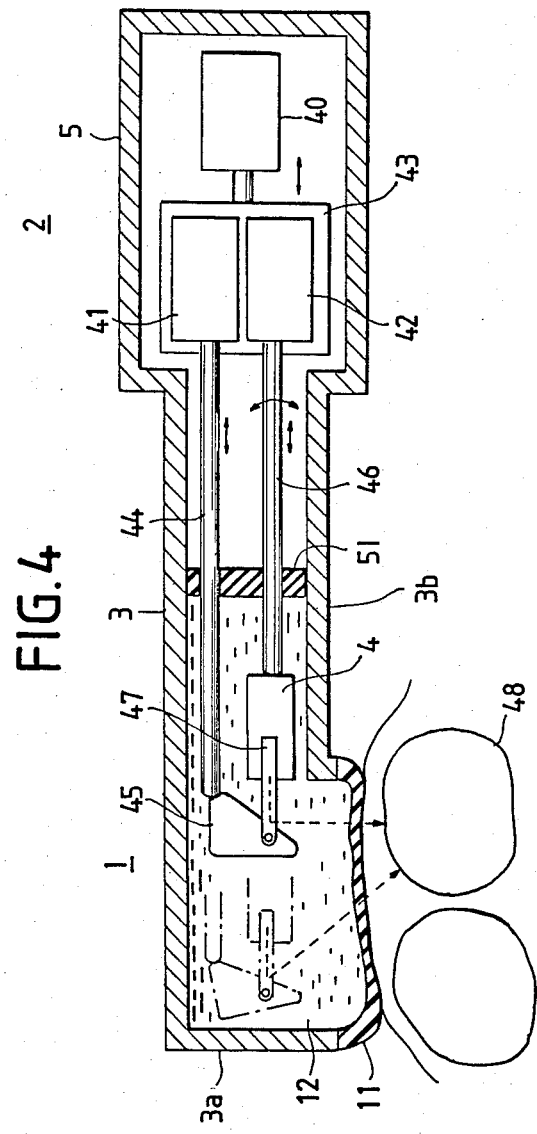
FIG.3
FIG.4

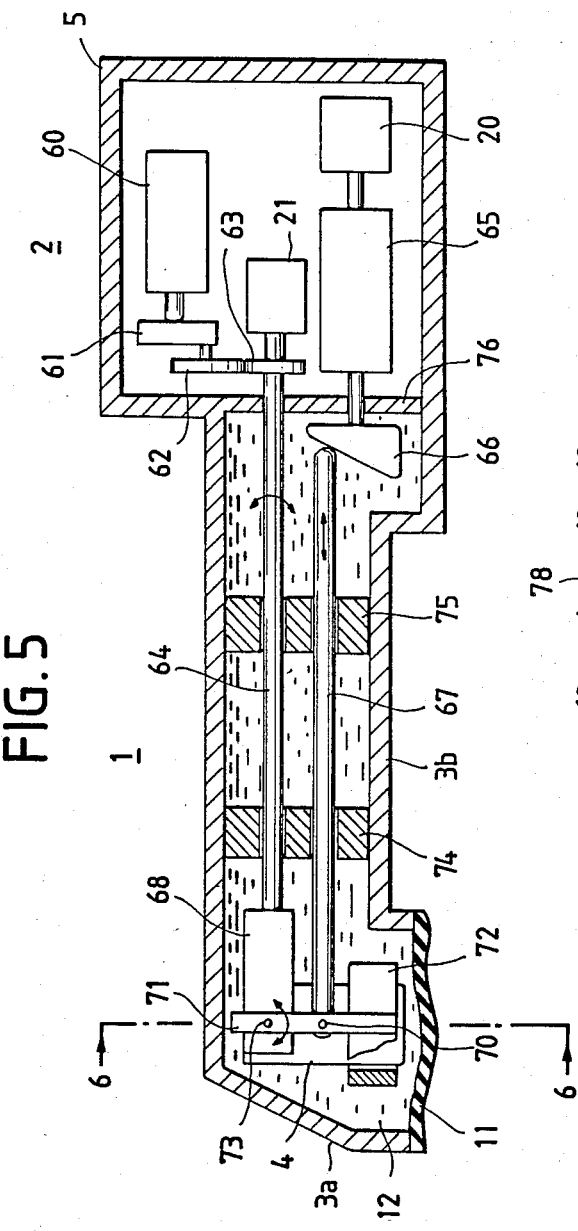
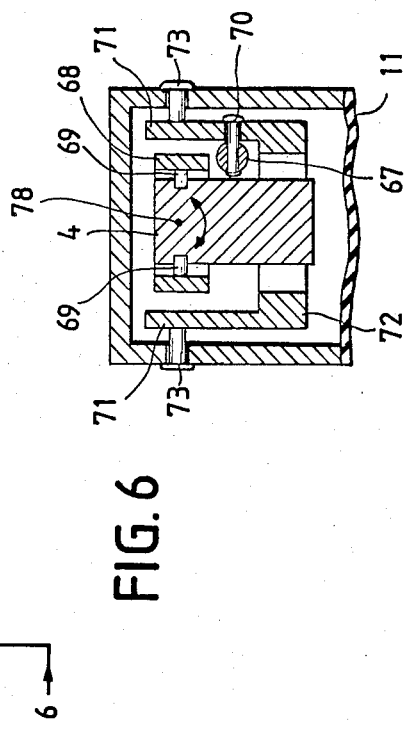
FIG. 5
FIG. 6

ULTRASONIC PROBE HAVING DUAL-MOTION TRANSDUCER

BACKGROUND OF THE INVENTION

This invention relates to mechanically scanned ultrasonic probe. The invention is particularly useful for dental applications.

A mechanically scanned ultrasonic diagnostic probe for use in dental clinics is shown and described in Japanese Laid-open Patent Publication 58-185139 (published Oct. 28, 1983). This ultrasonic probe includes a mechanism by which an ultrasonic transducer is arranged to swing about a drive shaft to steer the acoustic beam in a sector plane. However, it is desired to examine different portions of a patient's teeth at different angles to obtain as much data as possible. This requires that the probe be manually moved with precision. Because of the limitations on the range of angles in which the probe can be oriented and on the space available, difficulties have been encountered to manually control the position of the probe. It is further desirable that the size of the probe be as small as possible to permit it to reach the deeper area of the patient's teeth.

SUMMARY OF THE INVENTION

It is therefore an object of the present invention to provide an ultrasonic probe capable of generating acoustic data on three dimensions of an object under examination.

This object is attained by the provision of a dual motion drive mechanism located at one end of an elongated housing and a linkage that transmits the dual motion to an ultrasonic transducer located at the other end of the housing. An acoustic beam transmitted by the transducer is steered in orthogonal directions.

BRIEF DESCRIPTION OF THE DRAWINGS

The present invention will be described in further detail with reference to the accompanying drawings in which:

FIG. 1 is a cross-sectional view taken along the longitudinal axis of an ultrasonic probe according to a first embodiment of this invention;

FIG. 2 is a cross-sectional view taken along the lines 2—2 of FIG. 1;

FIG. 3 is an illustration of a modification of the first embodiment;

FIG. 4 is an illustration of a second embodiment of this invention;

FIG. 5 is an illustration of a third embodiment of this invention;

FIG. 6 is a cross-sectional view taken along the lines 6—6 of FIG. 5; and

DETAILED DESCRIPTION

Figure 7:
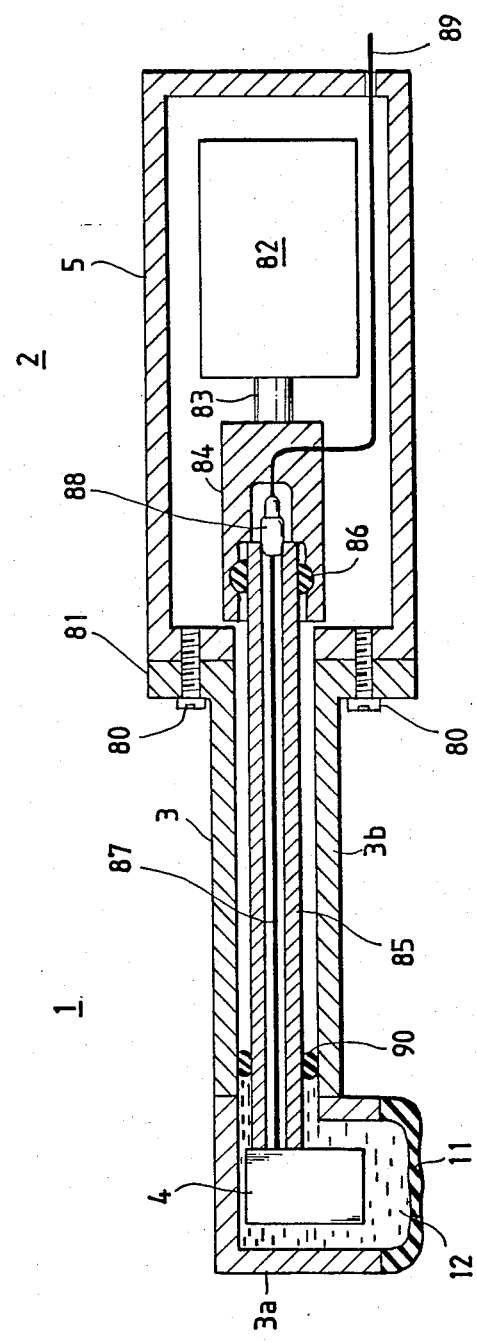
FIG. 7 is an illustration of a fourth embodiment of this invention.

Referring now to FIGS. 1 and 2, there is shown an ultrasonic probe according to a first embodiment of the invention. The probe is generally in the shape of a toothbrush and comprises a transducer section 1 and a dual motion drive section 2. Transducer section 1 is encased in a housing 3 having a downwardly flared, head portion 3a, which accomodates an ultrasonic transducer 4 and a hollow arm portion 3b connected to the drive section 2. The arm portion 3b has a sufficient length to allow the head portion to reach the innermost part of the patient's teeth. Dual motion drive section 2 is encased in a housing 5 which accommodates a dual motion drive mechanism. The housing 5 serves as a hand grip portion of the probe.

As is well known in the art, transducer 1 comprises an array of piezoelectric elements for emitting an acoustic beam 6 into an object 7 or teeth under examination when excited by drive pulses. The drive pulses are mutually phase-shifted so that the acoustic energies transmitted individually from the piezoelectric elements form an intensified narrow beam. The transducer also acts as a sensor during receive mode for converting echos from the object 7 to an electrical signal.

Transducer 4 is rotatably mounted by a pin 8 on the free end of a drive shaft 9. An arcuate guide arm 10 extends from one inner side wall of the housing portion 3a through an opening 4a of transducer 1 to the other inner side wall so that transducer 4 is swingable about guide arm 10 in a first plane and is further swingable about the axis of drive shaft 9 in a second plane normal to the first plane. Head portion 3a has a lower open end sealed fluid-tightly with a diaphragm 11 of a material which is transparent to acoustic energy and is flexible enough to take the shape of human teeth.

Head portion 3a is partially filled with liquid 12 in which the energy radiating face of transducer 4 is submerged. Liquid 12 is of a material which allows acoustic energy to propagate with a minimum loss and which provides acoustic impedance match between the transducer and object. One suitable material for the liquid is water. Liquid 12 is contained by a sealing member 13 which provides fluid-tight sealing between the housing's inner walls and the side walls of transducer 4. To permit transducer 4 to swing in the orthogonal directions, sealing member 13 is flexible and preferably formed into a corrugated, bellows-like shape.

The dual motion drive comprises a first micromotor 14 with its rotor shaft firmly coupled to a swash-plate cam 15 having its cam face in camming contact with a proximal end of drive shaft 9. A second micromoter 16 drives an eccentric cam 17 which translates the rotary motion to a swing motion, the latter being transmitted by a friction wheel 18 to a friction wheel 19 which is fixedly mounted on drive shaft 9. For purposes of detecting the accurate angular position of the micromotor 14, a potentiometer or angle sensor 20 is coupled to the shaft of motor 14. Likewise, the cam shaft of cam 17 is coupled by a similar potentiometer 21 to the friction wheel 18.

Drive shaft 9 therefore provides reciprocating and swing motions and transducer 4 swings about guide arm 10 in response to the reciprocation of drive shaft 9 and further swings about the axis of drive shaft 9 in response to the swing of the latter. The acoustic beam is thus steerable in a first sector plane parallel to the axis of drive shaft 9 and in a second sector plane normal to the first sector plane. Depending on the speeds of the reciprocating and swing motions relative to each other, the beam is steered along each of a plurality of scan lines and successively shifted to the next scan line as in a raster format. Three-dimensional diagnostic information is therefore obtained. The need for manually repositioning the probe is eliminated.

According to a feature of the invention, the orthogonal swing motions of the transducer permit it to be encased in a small space which advantageously reduces the probe size.

FIGS. 3 to 7 are illustrations of various modifications of the present invention in which parts corresponding to those in FIGS. 1 and 2 are marked with the same numerals and the descriptions thereof are omitted for brevity.

To permit access to side walls or roots of the innermost teeth, the head portion 3a is preferably bent with respect to the arm portion 3b as shown in FIG. 3. This is accomplished by dividing the drive shaft 9 into a shaft 9a connected to the drive section 2 and a shaft 9b swingably carrying the transducer 4 and coupling the shafts 9a and 9b by a flexible joint 30 such as flexible cable or universal joint.

It is also desired that acoustic energy be always directed toward the center of a tooth as the point of scan is shifted along the curvature of the tooth. This is accomplished by an embodiment shown in FIG. 4. This embodiment comprises a linear motor 41 and a rotary drive 42 which are fixedly mounted on a carriage 43. The rotary drive 42 includes a rotary motor and a cam arrangement that translates the rotary motion to a swing motion. This carriage is reciprocably moved by means of a common linear motor 40 to reciprocate transducer 4 across elongated acoustic window 11. The output shaft of linear motor 41 is connected to one end of a drive shaft 44, the other end of which is in abutment with an acoustic reflector 45. The output shaft of rotary motor 42 is fixedly connected by a drive shaft 46 to transducer 4.

Transducer 4 has a pair of arms 47 between which the reflector 45 is pivotably mounted and urged clockwise by a spring, not shown, toward drive shaft 44. The energy emitted from transducer 4 is reflected by reflector 45 toward the center of a tooth 48. All the components are encased in a toothbrush-like housing 49. Housing 49 is filled to a point halfway of its arm portion and fluid-tightly contained by a sealing member 51.

Transducer 4 and reflector 45 are caused to reciprocate by the common linear motor 40 and are rotated by swing motion drive 42, whereby the beam is scanned along a path parallel with the vertical axis of the tooth 48 in response to the swing motion and shifted to the next path in response to a displacement in the reciprocation.

Since drive shaft 44 is driven by linear motor 41 as well as by the common linear motor 40, it reciprocates slightly higher than the reciprocation of drive shaft 46. As a result, the angle of inclination of reflector 45 is varied as a function of distance away from the drive section so that the beam reflected upon it is automatically oriented toward the center of tooth 48 as indicated by chain-dot lines in FIG. 4.

An embodiment shown in FIGS. 5 and 6 is a further preferred form of the present invention. In this embodiment, the transducer's point of swing on the first plane coincides with its point of swing on the second plane. This coincidence is advantageous for the design of scan converters. This is accomplished by the provision of separate drive mechanisms for swing motion and reciprocation.

As in the first embodiment, swing motion is provided by a rotary motor 60 which drives eccentric cam 61 which translates the rotary motion to a swing motion, the latter being transmitted via friction wheels 62, 63 to a rotary drive shaft 64. Reciprocating motion is provided by a rotary motor 65 having its output fixedly coupled to swash-plate cam 66. A linear drive shaft 67 has its read end in contact with the cam face of the swash plate. Drive shafts 64 and 67 are journalled through a pair of supports 74 and 75.

Rotary drive shaft 64 is fixedly connected to the web portion of a first U-shaped support 68. Transducer 4 is pivotally mounted on support 68 by a pair of trunnions 69 which intersect the axis 78 of rotary drive shaft 64 as shown in FIG. 6. Linear drive shaft 67 is, on the other hand, connected by a pin 70 to one of a pair of side upright members 71 which form a second U-shaped member with a rectangular frame member 72 in which the lower part of transducer 4 is positioned. As shown in FIG. 6, the frame member 72 has a sufficient space therein in the transverse direction of the housing to give a desired swing motion to transducer 4. Upright members 71 are pivotally mounted by trunnions 73 to opposite inner side walls of the head portion 3a. The transducer section 1 of the probe is separated by a sealing member 76 from the drive section 2 and the transducer section 1 is filled with liquid 12.

It is seen that transducer 4 swings about axis 78 in response to the swing motion of rotary shaft 64. The reciprocating motion of linear drive shaft 67 causes frame member 72 to swing about trunnions 73 forcing transducer 4 to swing about trunnions 69. Since trunnions 69 coincide with the rotary axis 78, the transducer swings about a single pivot point in either direction of its orthogonal motions.

In this embodiment, swash-plate cam 66 is submerged in liquid 12. This reduces pressure variation in liquid 12 which would otherwise occur as a result of the reciprocation of shaft 67.

A further embodiment of the present invention is illustrated in FIG. 7. This embodiment facilitates servicing by making transducer section 1 and drive section 2 detachable from each other. Housing 5 of the drive section is secured by screws 80 to a flange 81 which forms part of the arm portion 3b. Dual motion drive mechanism 82 has an output shaft 83 fixed to an open-ended cylinder 84. Transducer 4 is attached to a front end of a hollow drive shaft 85 whose rear end is snugly and detachably engaged into the opening of cylinder 84 by a flexible ring 86. A signal transmission cable 87 extends from transducer 4 through drive shaft 85 to a connector 88 which connects the cable with a second cable 89 leading to control circuitry. A sealing member 90 is provided to contain liquid 12 in the head portion 3a. Head portion 3a is cemented to the front end of arm portion 3b.

When disassembling the probe, screws 80 are loosened and the drive section 2 is manually pulled in a direction away from arm portion 3b. Due to the detachable arrangement by which drive shaft 85 is connected to cylinder 84, these components are simultaneously disengaged from each other. At the same time the coupling elements of connector 88 are decoupled from each other.

The foregoing description shows only preferred embodiments of the preset invention. Various modifications are apparent to those skilled in the art without departing from the scope of the present invention which is only limited by the appended claims. Therefore, the embodiments shown and described are only illustrative, not restrictive.

What is claimed is:
1. An ultrasonic probe comprising:
   an elongated housing having an acoustic window at one end thereof;

an ultrasonic transducer located in said housing for emitting an acoustic beam through said acoustic window;

a dual motion drive means located at the other end of said housing for providing dual motions having a reciprocating motion and a swing motion transverse to the reciprocating motion; and means for coupling said drive means to said transducer to transmit thereto said dual motions so that said beam is steerable in orthogonal directions, wherein said coupling means comprises:

a drive shaft connected at one end to said dual motion drive means to transmit said reciprocating and swing motions to the other end thereof; and means for movably mounting said transducer at the other end of said drive shaft so that said transducer is swingable in a first plane in response to said reciprocating motion and in a second plane normal to said first plane in response to said swing motion, wherein said transducer is formed with an opening extending in the transverse direction of the housing, said mounting means comprising:

a pivot member extending through said transducer and said drive shaft in said transverse direction; and an arcuate guide member spaced from said pivot member, the guide member extending through said opening so that said transducer is swingable about said guide member in response to said reciprocating motion and further swingable about the axis of said drive shaft in response to said swing motion.

2. An ultrasonic probe as claimed in claim 1, wherein said transducer is oriented so that said beam is emitted at an angle to the longitudinal axis of said housing.

3. An ultrasonic probe as claimed in claim 1, wherein said housing comprises a head portion, a hand-grip portion and an arm portion therebetween, said arm and hand-grip portions being aligned longitudinally of said housing, said transducer being located in said head portion and said dual motion drive means being located in said hand-grip portion, said head portion being filled with acoustic energy transmitting liquid.

4. An ultrasonic probe as claimed in claim 1, wherein said acoustic window opens in a direction normal to the longitudinal axis of said housing.

5. An ultrasonic probe as claimed in claim 1, wherein said acoustic window comprises a diaphragm.

6. An ultrasonic probe as claimed in claim 1, further comprising a flexible sealing member for providing sealing with inner walls of said head portion and side walls of said transducer, the sealing member being located adjacent said arcuate guide member to define a chamber, said chamber being filled with liquid.

7. An ultrasonic probe as claimed in claim 6, wherein said sealing member is in the form of a corrugated, bellows-like shape.

8. An ultrasonic probe for dental diagnosis comprising:

a housing including a head portion having an acoustic window, a hand-grip portion and an arm portion connecting the head portion to the hand-grip portion, said head portion being at least partially filled with acoustic-energy transmitting liquid;

dual motion drive means in said hand-grip portion for providing dual motions having a first motion component in a longitudinal direction of said housing and a second motion component about said longitudinal direction;

an electroacoustic transducer in said head portion for emitting an acoustic beam through said acoustic window; and coupling means in said arm portion for coupling said dual motion drive means to said transducer for steering said beam in orthogonal directions in response to the first and second motion components, wherein said dual motion drive means comprises a rotary motor and a cam having an inclined cam face, said cam being connected to be driven by said motor, said couplind means comprising a shaft having one end thereof being in camming contact with said cam face, the other end of said shaft being pivotally connected to said transducer.

9. An ultrasonic probe as claimed in claim 8, wherein said acoustic window comprises a diaphragm.

10. An ultrasonic probe as claimed in claim 8, wherein said transducer comprises:

a block pivotally connected to the other end of said shaft, said block having an opening therein; and an arcuate guide extending through said opening so that said block is swingable about said guide in response to said first motion component and further swingable about the axis of said shaft in response to said second motion component.

11. An ultrasonic probe as claimed in claim 10, further comprising a flexible sealing member for providing sealing contact between inner walls of said head portion and side walls of said block to define a chamber in which said liquid is contained.

12. An ultrasonic probe as claimed in claim 11, wherein said sealing member is in the form of a corrugated, bellows-like shape.

* * * * *